US010203322B2

(12) United States Patent
Boutaud et al.

(10) Patent No.: US 10,203,322 B2
(45) Date of Patent: Feb. 12, 2019

(54) METHOD FOR IDENTIFYING SUBJECTS WITH INCREASED RISK OF ST-SEGMENT ELEVATION MYOCARDIAL INFARCTION (STEMI) AND IDENTIFYING SUBJECTS LIKELY TO RESPOND TO PARTICULAR TREATMENTS

(71) Applicant: Vanderbilt University, Nashville, TN (US)

(72) Inventors: Olivier Boutaud, Nashville, TN (US); Elias V. Haddad, Nashville, TN (US); Eitan Friedman, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 15/872,864

(22) Filed: Jan. 16, 2018

(65) Prior Publication Data
US 2018/0202998 A1 Jul. 19, 2018

Related U.S. Application Data

(60) Provisional application No. 62/446,187, filed on Jan. 13, 2017.

(51) Int. Cl.
*A61K 31/404* (2006.01)
*G01N 33/50* (2006.01)

(52) U.S. Cl.
CPC ....... *G01N 33/5091* (2013.01); *A61K 31/404* (2013.01); *G01N 2800/324* (2013.01); *G01N 2800/50* (2013.01); *G01N 2800/52* (2013.01)

(58) Field of Classification Search
CPC .................................................. A61K 31/404
See application file for complete search history.

(56) References Cited

PUBLICATIONS

Friedman et al., Understanding the role of prostaglandin E2 in regulating human platelet activity in health and disease, Thrombosis Research, vol. 136, Issue 3, Sep. 2015, pp. 493-503.*
Smith et al, PGE2 decreases reactivity of human platelets by activating EP2 and EP4, Thrombosis Research, vol. 126, Issue 1, Jul. 2010, pp. e23-e29.*
Kabbani, S.S., et al., Platelet reactivity characterized prospectively: a determinant of outcome 90 days after percutaneous coronary intervention. Circulation, 2001. 104(2): p. 181-6.
Trip, M.D., et al., Platelet hyperreactivity and prognosis in survivors of myocardial infarction. New England Journal of Medicine, 1990. 322(22): p. 1549-54.
Smith, J.P., et al., PGE2 decreases reactivity of human platelets by activating EP2 and EP4. Thrombosis Research, 2010. 126(1): p. e23-9.
Motoyama, S., et al., Computed tomographic angiography characteristics of atherosclerotic plaques subsequently resulting in acute coronary syndrome. J Am Coll Cardiol, 2009. 54(1): p. 49-57.
Berry, J.D., et al., Framingham risk score and prediction of coronary heart disease death in young men. Am Heart J, 2007. 154(1): p. 80-6.
Fuster, V., et al., The pathogenesis of coronary artery disease and the acute coronary syndromes (1). New England Journal of Medicine, 1992. 326(4): p. 242-50.
Fuster, V., et al., The pathogenesis of coronary artery disease and the acute coronary syndromes (2). New England Journal of Medicine, 1992. 326(5): p. 310-8.
Kabbani, S.S., et al., Usefulness of platelet reactivity before percutaneous coronary intervention in determining cardiac risk one year later. American Journal of Cardiology, 2003. 91(7): p. 876-8.
Ridker, P.M., J.E. Buring, and N. Rifai, Soluble P-selectin and the risk of future cardiovascular events. Circulation, 2001. 103(4): p. 491-5.
Thomas, M.R., et al., A platelet P-selectin test predicts adverse cardiovascular events in patients with acute coronary syndromes treated with aspirin and clopidogrel. Platelets, 2014. 25(8): p. 612-8.
Iyu, D., et al., PGE1 and PGE2 modify platelet function through different prostanoid receptors. Prostaglandins Other Lipid Mediat, 2011. 94(1-2): p. 9-16.
Schober, L.J., et al., The role of PGE(2) in human atherosclerotic plaque on platelet EP(3) and EP(4) receptor activation and platelet function in whole blood. J Thromb Thrombolysis, 2011. 32(2): p. 158-66.
Friedman, E.A., et al., Understanding the role of prostaglandin E2 in regulating human platelet activity in health and disease. Thromb Res, 2015. 136(3): p. 493-503.
Tilly, P., et al., Blocking the EP3 receptor for PGE2 with DG-041 decreases thrombosis without impairing haemostatic competence. Cardiovasc Res, 2014. 101(3): p. 482-91.
Fox, S.C., et al., Effects on platelet function of an EP3 receptor antagonist used alone and in combination with a P2Y12 antagonist both in-vitro and ex-vivo in human volunteers. Platelets, 2013. 24(5): p. 392-400.
Tantry, U.S., et al., Consensus and update on the definition of on-treatment platelet reactivity to adenosine diphosphate associated with ischemia and bleeding. J Am Coll Cardiol, 2013. 62(24): p. 2261-73.
Rieber, J., et al., Diagnostic accuracy of optical coherence tomography and intravascular ultrasound for the detection and characterization of atherosclerotic plaque composition in ex-vivo coronary specimens: a comparison with histology. Coron Artery Dis, 2006. 17(5): p. 425-30.

(Continued)

*Primary Examiner* — Svetlana M Ivanova
(74) *Attorney, Agent, or Firm* — Stites & Harbison PLLC; Mandy Wilson Decker

(57) ABSTRACT

A method for identifying an increased risk of developing ST-Segment Elevation Myocardial Infarction (STEMI) in a subject involves obtaining a platelet-containing plasma sample from the subject; determining a Prostaglandin E2 (PGE2) phenotype of the platelets of the subject; and identifying the subject has having an increased risk of developing STEMI when the subject has a potentiating phenotype, as compared to the risk of a subject having an inhibitory phenotype.

8 Claims, 3 Drawing Sheets

(56) References Cited

PUBLICATIONS

Folsom, A.R., et al., Association of hemostatic variables with prevalent cardiovascular disease and asymptomatic carotid artery atherosclerosis. The Atherosclerosis Risk in Communities (ARIC) Study Investigators. Arterioscler Thromb, 1993. 13(12): p. 1829-36.
O'Gara, et al., 2013 ACCF/AHA Guidelines for the Management of ST-Elevation Myocardial Infarction, J. Am. College of Cardiology, 2013. 61(61): e78-140.
Greenland, et al., 2010 ACCF/AHA Guideline for Assessment of Cardiovascular Risk in Asymptomatic Adults, J. Am. College of Cardiology, 2010. 56(25): e50-103.
Eckel, et al., 2013 AHA/ACC Guideline Lifestyle Management to Reduce Cardiovascular Risk, J. Am. College of Cardiology, 2014. 63(25): 2960-84.
Levine, et al., 2015 ACC/AHA/SCAI Focused Update on Primary Percutaneous Coronary Intervention for Patients with ST-Elevation Myocardial Infarction, 2016. 67(10): 1235-1250.
Thompson, S.G., et al., Hemostatic factors and the risk of myocardial infarction or sudden death in patients with angina pectoris. European Concerted Action on Thrombosis and Disabilities Angina Pectoris Study Group. N Engl J Med, 1995. 332(10): p. 635-41.

\* cited by examiner

METHOD FOR IDENTIFYING SUBJECTS WITH INCREASED RISK OF ST-SEGMENT ELEVATION MYOCARDIAL INFARCTION (STEMI) AND IDENTIFYING SUBJECTS LIKELY TO RESPOND TO PARTICULAR TREATMENTS

RELATED APPLICATIONS

This application claims priority from U.S. Provisional Application Ser. No. 62/446,187 filed Jan. 13, 2017, the entire disclosure of which is incorporated herein by this reference.

GOVERNMENT INTEREST

This invention was made with government support under grant numbers HL081009 and 5T32HL007411 awarded by the National Institutes of Health. The government has certain rights in the invention.

TECHNICAL FIELD

The presently-disclosed subject matter generally relates to predicting risk of developing ST-Segment Elevation Myocardial Infarction (STEMI) in a subject, and to identifying candidate subjects likely to respond to particular treatments for STEMI.

INTRODUCTION

Despite significant advances in cardiovascular (CV) disease prevention, there remains a significant incidence of acute coronary syndrome that is not adequately anticipated by current risk prediction tools. In particular, composite risk assessment scores, such as the Framingham risk score, are not able to predict events in many patients who develop ST-Segment Elevation Myocardial Infarction (STEMI) [1, 2].

Furthermore, it is understood that patients with high platelet reactivity in the setting of antiplatelet therapy ("on-treatment") are at increased risk for primary or recurrent myocardial infarction, thrombotic complications following percutaneous coronary intervention (PCI), and overall cardiovascular mortality [1-5]. However, markers of intrinsic platelet reactivity have yet to be incorporated into personalized risk prediction. In light of this, there has been considerable interest in novel methods to identify the vulnerable patient based on specific characteristics of thrombosis elements.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes method for identifying subjects with increased risk of ST-Segment Elevation Myocardial Infarction (STEMI). The presently-disclosed subject matter also includes a method of identifying subjects likely to respond to treatment for STEMI. The presently-disclosed subject matter also includes a method of treating STEMI in a subject.

In some embodiments, a method of identifying an increased risk of developing STEMI in a subject involves (a) obtaining a platelet-containing plasma sample from the subject; (b) determining a Prostaglandin E2 (PGE2) phenotype of the platelets of the subject; and (c) identifying the subject has having an increased risk of developing STEMI when the subject has a potentiating phenotype, as compared to the risk of a subject having an inhibitory phenotype. Determining a phenotype can involve (i) contacting a first portion of the plasma sample with a thromboxane agonist (such as U46,619); (ii) contacting a second portion of the plasma sample with the thromboxane agonist and PGE2; (iii) comparing the platelet aggregation in the first portion of the plasma sample to the platelet aggregation in the second portion of the plasma sample; and (iv) identifying the subject has having an inhibitory phenotype if the PGE2 inhibits platelet aggregation, or identifying the subject as having a potentiating phenotype if the PGE2 potentiates platelet aggregation.

In some embodiments of the method, when the subject has a potentiating phenotype, the method can also involve: (a) contacting a third portion of the plasma sample with an EP3 antagonist and the thromboxane agonist; (b) contacting a fourth portion of the plasma sample with the EP3 antagonist, the thromboxane agonist, and PGE2; (c) comparing the platelet aggregation in the third portion of the plasma sample to the platelet aggregation in the fourth portion of the plasma sample; and (d) determining whether the potentiating phenotype has shifted to an inhibitory phenotype. When the potentiating phenotype shifts to an inhibitory phenotype the subject is identified as a candidate for treatment. In some embodiments of the method, the EP3 antagonist is contacted to the fourth portion of the plasma sample is selected from the group consisting of: L-826266, ONO-AE3-240, L-798, 106, L-826266, ONO-AE2-227, ONO-AE3-208, ONO-8711, SC-51322, AH6809, ONO-8713, ONO-AE5-599, ONO-AE3-240, ONO-AE2-227, and DG-041.

In some embodiments of the method, when treatment is administered to the candidate subject. Such treatment can include an EP3 antagonist, such as DG-041. Other treatments could include, for example, lifestyle modification, such as not smoking, proper diet, exercise; management of cholesterol through pharmaceutical or other treatment; management of blood pressure using pharmaceutical or other treatment methods; use of aspirin in select populations where the risk of bleeding does not outweigh the benefit, e.g., diabetics population. Other exemplary treatments are outlined in: O'Gara, et al., 2013 *ACCF/AHA Guidelines for the Management of ST-Elevation Myocardial Infarction*, J. Am. College of Cardiology, 2013. 61(61): e78-140; Levine, et al., 2015 *ACC/AHA/SCAT Focused Update on Primary Percutaneous Coronary Intervention for Patients with ST-Elevation Myocardial Infarction*, J. Am. College of Cardiology, 2015. 67(10): 1235-1250; Greenland, et al., 2010 *ACCF/AHA Guideline for Assessment of Cardiovascular Risk in Asymptomatic Adults*, J. Am. College of Cardiology, 2010. 56(25): e50-103; Eckel, et al., 2013 *AHA/ACC Guideline Lifestyle Management to Reduce Cardiovascular Risk*, J. Am. College of Cardiology, 2014. 63(25): 2960-84; and Levine, et al., 2015 *ACC/AHA/SCAT Focused Update on Primary Percutaneous Coronary Intervention for Patients with ST-Elevation Myocardial Infarction,* 2016. 67(10): 1235-1250, which are incorporated herein by this reference.

As will be appreciated by the skilled artisan, in some embodiments, the method is useful for excluding the subject as a candidate for treatment when the potentiating phenotype does not shift to an inhibitory phenotype. In this regard, a subject for whom a treatment would not or would have a limited or low likelihood of being useful would not be subjected to receiving unnecessary treatment.

The presently-disclosed subject matter further includes a method of identifying a candidate subject likely to respond to STEMI treatment, which involves (a) obtaining a platelet-containing plasma sample from a subject having a potentiating phenotype; (b) contacting a first portion of the plasma sample with an EP3 antagonist and the thromboxane agonist; (c) contacting a second portion of the plasma sample with the EP3 antagonist, the thromboxane agonist, and PGE2; (d) comparing the platelet aggregation in the first portion of the plasma sample to the platelet aggregation in the second portion of the plasma sample; and (e) identifying the subject as a candidate for treatment when the PGE2 inhibits platelet aggregation, indicating a shift from the potentiating phenotype to an inhibitory phenotype; and excluding the subject as a candidate for treatment when the PGE 2 fails to inhibit platelet aggregation. The EP3 antagonist contacted to the second portion of the plasma sample can be selected from the group consisting of: L-826266, ONO-AE3-240, L-798,106, 826266, ONO-AE2-227, ONO-AE3-208, ONO-8711, SC-51322, AH6809, ONO-8713, ONO-AE5-599, ONO-AE3-240, ONO-AE2-227, and DG-041.

In some embodiments of the method, determining whether the subject has a potentiating phenotype involves (i) contacting a first portion of the plasma sample with a thromboxane agonist; (ii) contacting a second portion of the plasma sample with the thromboxane agonist and PGE2; (iii) comparing the platelet aggregation in the first portion of the plasma sample to the platelet aggregation in the second portion of the plasma sample; and (iv) identifying the subject has having an inhibitory phenotype if the PGE2 inhibits platelet aggregation, or identifying the subject as having a potentiating phenotype if the PGE2 potentiates platelet aggregation.

The method can further involve administering treatment to the subject when the subject is identified as a candidate for treatment Such treatment can include, for example, administering an EP3 antagonist, such as DG-041. Other exemplary treatments are outlined in: O'Gara, et al., Levine, et al., Greenland, et al., Eckel, et al., and Levine, et al.[29-33], which are incorporated herein by this reference.

The presently disclosed subject matter further includes a method of treating STEMI in a subject, which involves (a) obtaining a platelet-containing plasma sample from the subject; (b) determining a Prostaglandin E2 (PGE2) phenotype of the platelets of the subject; (c) identifying the subject has having an increased risk of developing STEMI when the subject has a potentiating phenotype, as compared to the risk of a subject having an inhibitory phenotype; and (d) administering treatment for treatment of STEMI when the subject has a potentiating phenotype.

In some embodiments, determining a Prostaglandin E2 (PGE2) phenotype of the platelets of the subject involves (i) contacting a first portion of the plasma sample with a thromboxane agonist; (ii) contacting a second portion of the plasma sample with the thromboxane agonist and PGE2; (iii) comparing the platelet aggregation in the first portion of the plasma sample to the platelet aggregation in the second portion of the plasma sample; and (iv) identifying the subject has having an inhibitory phenotype if the PGE2 inhibits platelet aggregation, or identifying the subject as having a potentiating phenotype if the PGE2 potentiates platelet aggregation.

In some embodiments, when the subject has a potentiating phenotype, the method also involves (a) contacting a third portion of the plasma sample with an EP3 antagonist and the thromboxane agonist; (b) contacting a fourth portion of the plasma sample with the EP3 antagonist, the thromboxane agonist, and PGE2; (c) comparing the platelet aggregation in the third portion of the plasma sample to the platelet aggregation in the fourth portion of the plasma sample; (d) determining whether the potentiating phenotype has shifted to an inhibitory phenotype; and (e) identifying the subject as being a candidate for treatment when the potentiating phenotype shifts to an inhibitory phenotype. In some embodiments, the EP3 antagonist contacted to the fourth portion of the plasma sample is selected from the group consisting of: L-826266, ONO-AE3-240, L-798,106, L-826266, ONO-AE2-227, ONO-AE3-208, ONO-8711, SC-51322, AH6809, ONO-8713, ONO-AE5-599, ONO-AE3-240, ONO-AE2-227, and DG-041.

The method can further involve administering treatment to the subject when the subject is identified as a candidate for treatment Such treatment can include, for example, administering an EP3 antagonist, such as DG-041. Other exemplary treatments are outlined in: O'Gara, et al., Levine, et al., Greenland, et al., Eckel, et al., and Levine, et al.[29-33], which are incorporated herein by this reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

DESCRIPTION OF EXEMPLARY EMBODIMENTS

Figure 1:
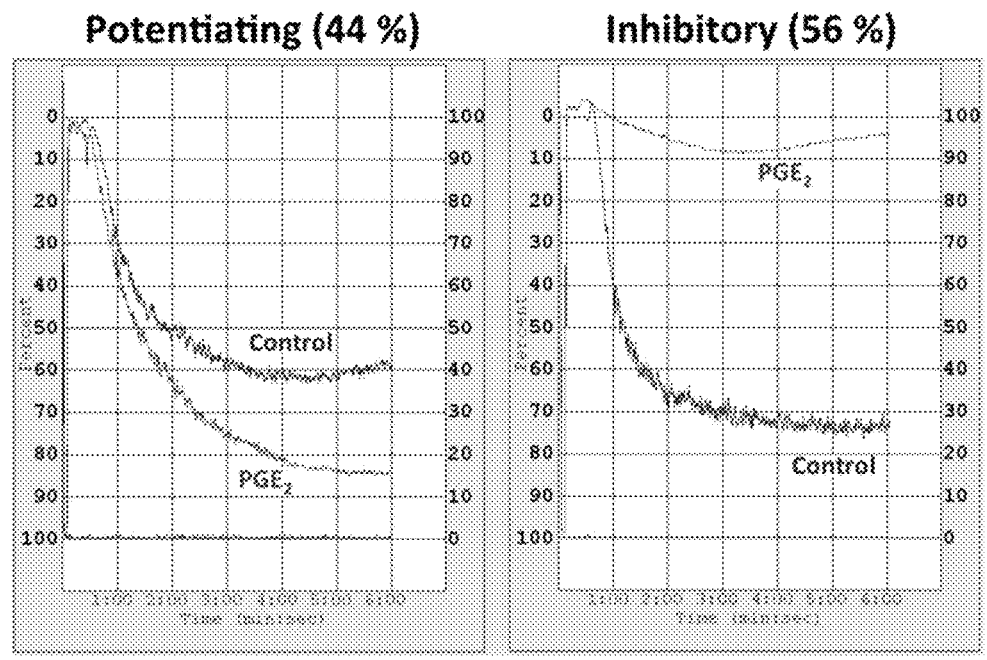
FIG. 1 includes representative traces of the two phenotypic groups analyzed by light transmission aggregometry. Platelet rich plasma (PRP) was preincubated with PGE2 100 nmol/L (PGE2) or vehicle (control) for 30 s, followed by a sub-maximal concentration of U46,619. Aggregation was recorded for 6 min. The frequency of each phenotypic group is indicated (n=86).

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter is related to methods of determining a probability or increased risk of developing ST-Segment Elevation Myocardial Infarction (STEMI), identifying candidates for treatment, and treating a subject. The methods disclosed herein involve determining a Prostaglandin E2 (PGE2) phenotype of platelets of the subject. Such phenotype can be determined by using a platelet-containing plasma sample from the subject. For example, platelet rich plasma, sometimes referred to as PRP in the literature and art, can be used. Platelet rich plasma can be obtained by centrifuging blood to remove red and white blood cells, as will be understood by those of ordinary skill in the art.

Prostaglandin E2 (PGE2) phenotype include an "inhibitory phenotype" and a "potentiating phenotype." The phenotypes can also be referred to as a "high threshold" phenotype" and a "low threshold phenotype." While inhibitory and high can be used quite interchangeably, and potentiating and low can be used quite interchangeably, as will be recognized by those of ordinary skill in the art, the low/high threshold terms refer to platelet reactivity, while the inhibitory/potentiating can refer to platelet function. However, as used herein, inhibitory phenotype and high phenotype are used interchangeably to refer to platelet aggregation that is inhibited by PGE2 in a platelet-containing plasma sample. Similarly, potentiating phenotype and low threshold phenotype are used interchangeably to refer to platelet aggregation that is potentiated by PGE2 in a platelet-containing plasma sample.

As disclosed herein, patients with lower thresholds for platelet activation are at increased risk for primary and recurrent myocardial infarction (MI) and overall cardiovascular (CV) mortality. The present inventors have demonstrated that there are two phenotypes of platelet response to Prostaglandin E2 (PGE2), such that it increases threshold for aggregation in approximately half of individuals (inhibitory) and lowers threshold for aggregation in approximately half of individuals (potentiating). As PGE2 is present in atherosclerotic plaques, and its receptors are present on platelets, biologic variability in PGE2 responses may have clinical implications. The present inventors contemplate that patients with higher thresholds for platelet activation, have a lower risk of thrombotic CV events, specifically ST-Elevation MI (STEMI).

The present inventors preformed studies, including an exemplary studies in which patients undergoing percutaneous coronary intervention for stable or unstable coronary disease were phenotyped for PGE2 response. Platelet rich plasma was treated with various concentrations of U46,619 (thromboxane agonist) with or without PGE2 100 nM, and phenotype determined by light aggregometry. Analysis of the maximum PGE2 effect (maximum aggregation with PGE2 minus maximum aggregation without it) was performed using linear and non-linear statistical methods.

Traditional cardiovascular risk factors were similar between groups. A higher percentage of patients with the potentiating phenotype had a history of STEMI than those with the inhibitory phenotype (See Examples). Logistic regression using restricted cubic spline showed that the predicted probabilities of STEMI increased from the strongest inhibitory phenotype to potentiating phenotypes.

PGE2 inhibitory phenotype confers an decreased lifetime risk of STEMI in individuals with high risks for CV events. The present inventors have shown that an EP3 receptor antagonist converts the potentiating to the inhibitory phenotype. Thus, the PGE2 phenotype is disclosed herein as a unique marker of cardiovascular risk and for identifying patients who would benefit from EP3 antagonist treatment.

The term "increased risk" is used herein to refer to those subjects whose likelihood of developing STEMI in their lifetime is increased, as compared to a normal subject. As will be appreciated by one of ordinary skill in the art, an increased risk is assessed relative to a control, and is a predictive, not an absolute, determination.

As used herein, the terms "treatment" or "treating" relate to any treatment of STEMI and include, for example, ameliorating or relieving the symptoms. As will be understood by those of ordinary skill in the art, when the term "prevent" or "prevention" is used in connection with a prophylactic treatment, it should not be understood as an absolute term that would preclude any sign of any sign of STEMI in a subject. Rather, as used in the context of prophylactic treatment, the term "prevent" can refer to inhibiting the development of STEMI, such as in a subject who may be at an increased risk of developing STEMI, but who has not yet been diagnosed as having it, limiting the severity of STEMI, arresting the development of STEMI, and the like.

The presently-disclosed subject matter includes method for identifying subjects with increased risk of ST-Segment Elevation Myocardial Infarction (STEMI). The presently-disclosed subject matter also includes a method of identifying subjects likely to respond to treatment for STEMI. The presently-disclosed subject matter also includes a method of treating STEMI in a subject.

In some embodiments, a method of identifying an increased risk of developing STEMI in a subject involves (a) obtaining a platelet-containing plasma sample from the subject; (b) determining a Prostaglandin E2 (PGE2) phenotype of the platelets of the subject; and (c) identifying the subject has having an increased risk of developing STEMI when the subject has a potentiating phenotype, as compared to the risk of a subject having an inhibitory phenotype. Determining a phenotype can involve (i) contacting a first portion of the plasma sample with a thromboxane agonist; (ii) contacting a second portion of the plasma sample with the thromboxane agonist and PGE2; (iii) comparing the platelet aggregation in the first portion of the plasma sample to the platelet aggregation in the second portion of the plasma sample; and (iv) identifying the subject has having an inhibitory phenotype if the PGE2 inhibits platelet aggregation, or identifying the subject as having a potentiating phenotype if the PGE2 potentiates platelet aggregation.

In some embodiments of the method, when the subject has a potentiating phenotype, the method can also involve: (a) contacting a third portion of the plasma sample with an EP3 antagonist and the thromboxane agonist; (b) contacting a fourth portion of the plasma sample with the EP3 antagonist, the thromboxane agonist, and PGE2; (c) comparing the platelet aggregation in the third portion of the plasma sample to the platelet aggregation in the fourth portion of the plasma sample; and (d) determining whether the potentiating phenotype has shifted to an inhibitory phenotype. When the potentiating phenotype shifts to an inhibitory phenotype the subject is identified as a candidate for treatment. In some embodiments of the method, the EP3 antagonist is contacted to the fourth portion of the plasma sample is selected from the group consisting of: L-826266, ONO-AE3-240, L-798, 106, L-826266, ONO-AE2-227, ONO-AE3-208, ONO-8711, SC-51322, AH6809, ONO-8713, ONO-AE5-599, ONO-AE3-240, ONO-AE2-227, and DG-041.

In some embodiments of the method, when treatment is administered to the candidate subject. Such treatment can include an EP3 antagonist, such as DG-041. Other treatments could include, for example, lifestyle modification, such as not smoking, proper diet, exercise; management of cholesterol through pharmaceutical or other treatment; management of blood pressure using pharmaceutical or other treatment methods; use of aspirin in select populations where the risk of bleeding does not outweigh the benefit, e.g., diabetics population. Other exemplary treatments are outlined in: O'Gara, et al., 2013 *ACCF/AHA Guidelines for the Management of ST-Elevation Myocardial Infarction*, J. Am. College of Cardiology, 2013. 61(61): e78-140; Levine, et al., 2015 *ACC/AHA/SCAT Focused Update on Primary Percutaneous Coronary Intervention for Patients with ST-Elevation Myocardial Infarction*, J. Am. College of Cardiology, 2015. 67(10): 1235-1250; Greenland, et al., 2010 *ACCF/AHA Guideline for Assessment of Cardiovascular Risk in Asymptomatic Adults*, J. Am. College of Cardiology, 2010. 56(25): e50-103; Eckel, et al., 2013 *AHA/ACC Guideline Lifestyle Management to Reduce Cardiovascular Risk*, J. Am. College of Cardiology, 2014. 63(25): 2960-84; and Levine, et al., 2015 *ACC/AHA/SCAT Focused Update on Primary Percutaneous Coronary Intervention for Patients with ST-Elevation Myocardial Infarction*, 2016. 67(10): 1235-1250, which are incorporated herein by this reference.

As will be appreciated by the skilled artisan, in some embodiments, the method is useful for excluding the subject as a candidate for treatment when the potentiating phenotype does not shift to an inhibitory phenotype. In this regard, a subject for whom a treatment would not or would have a limited or low likelihood of being useful would not be subjected to receiving unnecessary treatment.

The presently-disclosed subject matter further includes a method of identifying a candidate subject likely to respond to STEMI treatment, which involves (a) obtaining a platelet-containing plasma sample from a subject having a potentiating phenotype; (b) contacting a first portion of the plasma sample with an EP3 antagonist and the thromboxane agonist; (c) contacting a second portion of the plasma sample with the EP3 antagonist, the thromboxane agonist, and PGE2; (d) comparing the platelet aggregation in the first portion of the plasma sample to the platelet aggregation in the second portion of the plasma sample; and (e) identifying the subject as a candidate for treatment when the PGE2 inhibits platelet aggregation, indicating a shift from the potentiating phenotype to an inhibitory phenotype; and excluding the subject as a candidate for treatment when the PGE 2 fails to inhibit platelet aggregation. The EP3 antagonist contacted to the second portion of the plasma sample can be selected from the group consisting of: L-826266, ONO-AE3-240, L-798,106, 826266, ONO-AE2-227, ONO-AE3-208, ONO-8711, SC-51322, AH6809, ONO-8713, ONO-AE5-599, ONO-AE3-240, ONO-AE2-227, and DG-041.

In some embodiments of the method, determining whether the subject has a potentiating phenotype involves (i) contacting a first portion of the plasma sample with a thromboxane agonist; (ii) contacting a second portion of the plasma sample with the thromboxane agonist and PGE2; (iii) comparing the platelet aggregation in the first portion of the plasma sample to the platelet aggregation in the second portion of the plasma sample; and (iv) identifying the subject has having an inhibitory phenotype if the PGE2 inhibits platelet aggregation, or identifying the subject as having a potentiating phenotype if the PGE2 potentiates platelet aggregation.

The method can further involve administering treatment to the subject when the subject is identified as a candidate for treatment Such treatment can include, for example, administering an EP3 antagonist, such as DG-041. Other exemplary treatments are outlined in: O'Gara, et al., Levine, et al., Greenland, et al., Eckel, et al., and Levine, et al.[29-33], which are incorporated herein by this reference.

The presently disclosed subject matter further includes a method of treating STEMI in a subject, which involves (a) obtaining a platelet-containing plasma sample from the subject; (b) determining a Prostaglandin E2 (PGE2) phenotype of the platelets of the subject; (c) identifying the subject has having an increased risk of developing STEMI when the subject has a potentiating phenotype, as compared to the risk of a subject having an inhibitory phenotype; and (d) administering treatment for treatment of STEMI when the subject has a potentiating phenotype.

In some embodiments, determining a Prostaglandin E2 (PGE2) phenotype of the platelets of the subject involves (i) contacting a first portion of the plasma sample with a thromboxane agonist; (ii) contacting a second portion of the plasma sample with the thromboxane agonist and PGE2; (iii) comparing the platelet aggregation in the first portion of the plasma sample to the platelet aggregation in the second portion of the plasma sample; and (iv) identifying the subject has having an inhibitory phenotype if the PGE2 inhibits platelet aggregation, or identifying the subject as having a potentiating phenotype if the PGE2 potentiates platelet aggregation.

In some embodiments, when the subject has a potentiating phenotype, the method also involves (a) contacting a third portion of the plasma sample with an EP3 antagonist and the thromboxane agonist; (b) contacting a fourth portion of the plasma sample with the EP3 antagonist, the thromboxane agonist, and PGE2; (c) comparing the platelet aggregation in the third portion of the plasma sample to the platelet aggregation in the fourth portion of the plasma sample; (d) determining whether the potentiating phenotype has shifted to an inhibitory phenotype; and (e) identifying the subject as being a candidate for treatment when the potentiating phenotype shifts to an inhibitory phenotype. In some embodiments, the EP3 antagonist contacted to the fourth portion of the plasma sample is selected from the group consisting of: L-826266, ONO-AE3-240, L-798,106, L-826266, ONO-AE2-227, ONO-AE3-208, ONO-8711, SC-51322, AH6809, ONO-8713, ONO-AE5-599, ONO-AE3-240, ONO-AE2-227, and DG-041.

The method can further involve administering treatment to the subject when the subject is identified as a candidate for treatment Such treatment can include, for example, administering an EP3 antagonist, such as DG-041. Other exemplary treatments are outlined in: O'Gara, et al., Levine, et al., Greenland, et al., Eckel, et al., and Levine, et al.[29-33], which are incorporated herein by this reference.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

EXAMPLES

Figure 2:
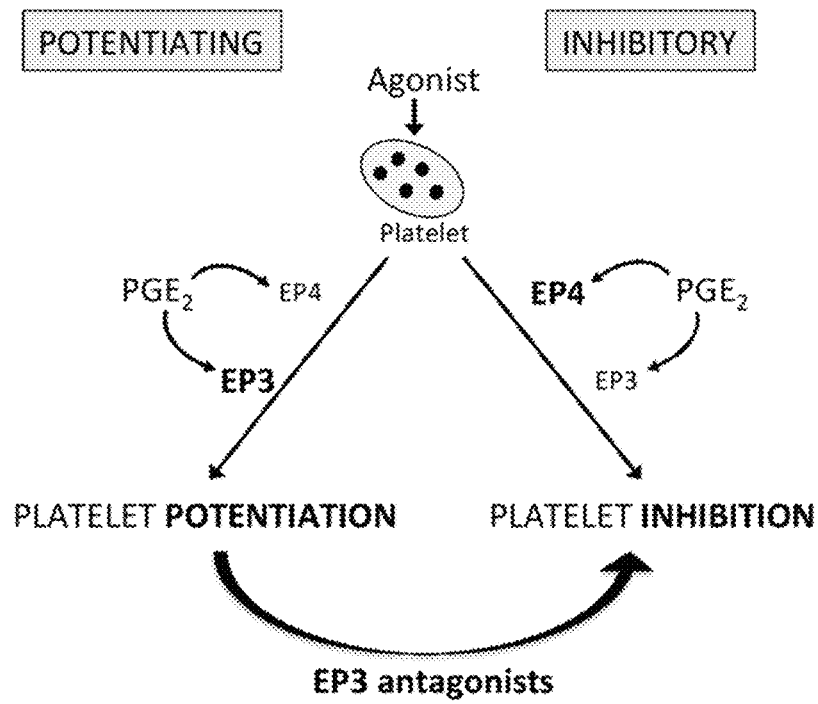
FIG. 2 is a pictorial representations of the effect of PGE2 on platelet activation in humans, where the net effect of PGE2 reflects the differential activation of the two receptors EP3 and EP4; EP3 antagonists shift phenotype from potentiating to inhibitory.

Prostaglandin E2 (PGE2) is an endogenous substance produced by macrophages in atherosclerotic plaques and by activated platelets [6]. In healthy volunteers, PGE2 increases the threshold of platelet activation by the thromboxane agonist U46,619 in 44% of individuals (potentiating phenotype) and decreases this threshold in 56% (inhibitory phenotype) (FIG. 1). These effects result from the net activation of two PGE2 receptor subtypes, EP3 and EP4. Further, an EP3 antagonist can shift phenotype from potentiating to inhibitory (FIG. 2). The present inventors contemplated that individuals with the potentiating phenotype, who have lower thresholds to platelet activation, would be at greater risk for STEMI.

Methods:
Patients and Blood Collection

The study was approved by the Vanderbilt University Institutional Review Board. Eighty-six patients were enrolled, who were undergoing percutaneous coronary intervention in the Vanderbilt cardiac catheterization laboratory for stable or unstable coronary artery disease. All patients provided informed written consent. Clinical data, including the presence or absence of a history of STEMI, was obtained from patient history and chart review. Presence of STEMI was confirmed by review of primary data including electrocardiograms and biomarkers. Blood was drawn from either a pre-existing intravenous catheter or a 19-gauge venipuncture needle. The first 3 mL was discarded before drawing blood into tubes containing 3.2% sodium citrate. Blood was centrifuged at 190×g for 10 minutes at room temperature, and the platelet-rich plasma (PRP) was transferred to a polypropylene container. The residual blood was centrifuged at 2000×g for 10 minutes, and the platelet poor-plasma was transferred to a separate polypropylene container.

Platelet Phenotyping

Measurements of platelet aggregation in PRP were made using light transmission aggregometry using a Chrono-Log lumi-aggregometer (Model 460VS). The aggregometer was calibrated for each sample to read 0-10% light transmission for PRP and 90-100% light transmission for PPP. Aliquots of PRP were placed in siliconized glass cuvettes containing Teflon-coated stir bars and incubated for 2 minutes at 37° C. PRP was preincubated with or without 100 nM PGE2 for 10-20 s before adding U46,619 at various concentrations. Samples were stirred at 800 rpm throughout a 6 minute aggregation run. Experiments were completed within 2 hours of phlebotomy. Percentage aggregation was recorded with Aggrolink software (Chrono-Log) and exported to GraphPad Prism for analysis. For each subject, multiple doses of U46,619 agonist were used to construct a dose response curve according to methods described previously [6]; each U46,619 dose was tested with and without PGE2.

In order to describe the phenotypic observation in a quantitative rather than just qualitative format a continuous variable was constructed as follows: for each dose of U46,619, the aggregation value obtained at the end of the 6 min run in the presence of PGE2 was subtracted from the value obtained without PGE2. The largest difference was reported as the maximum PGE2 effect (maximum difference). If the maximum difference was negative, the patient was classified in the inhibitory phenotype; if the maximum difference was positive, the patient was classified in the potentiating group. This variable is described as the maximum aggregation difference.

Statistical Analysis

Patient characteristics including traditional cardiovascular risk factors and demographics were compared between the two phenotypic groups using Pearson's Chi-square tests (for categorical variables) or Wilcoxon rank-sum test (for continuous variables) to examine if there were significant differences by phenotype.

Second, univariate logistic regressions were conducted to examine if there were significant associations between STEMI and traditional CV risk factors and PGE2 response phenotype. Odds Ratio (OR) and its 95% confidence interval (95% CI) were reported.

Figure 6:
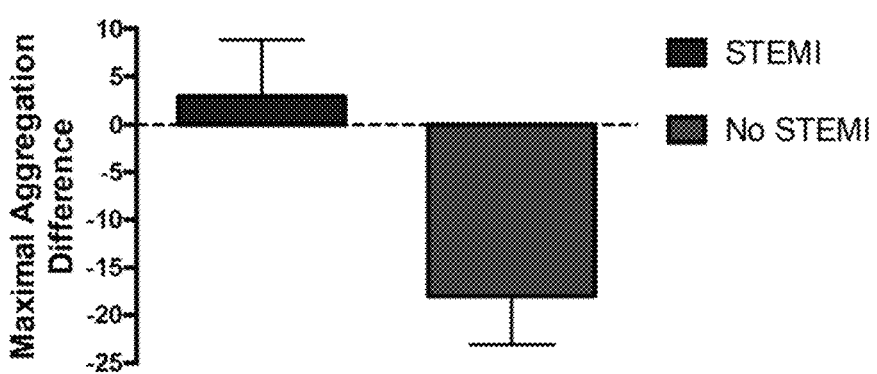
FIG. 6 illustrates a maximal aggregation difference between PGE2 and Vehicle, where a more negative value indicates a greater degree of inhibition and where the data plotted is mean and standard error (n≥31).

A multiple logistic regression model was used to assess the association of the maximum PGE2 effect (described as maximum aggregation difference (FIG. 6)) as a continuous variable and STEMI, while controlling for Diabetes Mellitus and smoking status. Restricted cubic spline was applied to capture potential non-linear relationship between phenotype and STEMI. Three knots were set at default locations (i.e., 10, 50 and 90 quantiles of the distribution of phenotype) because the sample size was less than 100.

Figure 3:
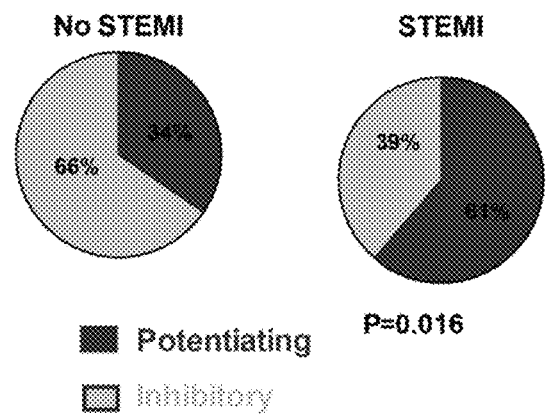
FIG. 3 illustrates the frequency of the potentiating phenotype and the inhibitory phenotype in patients with or without a history of STEMI.
Figure 4:
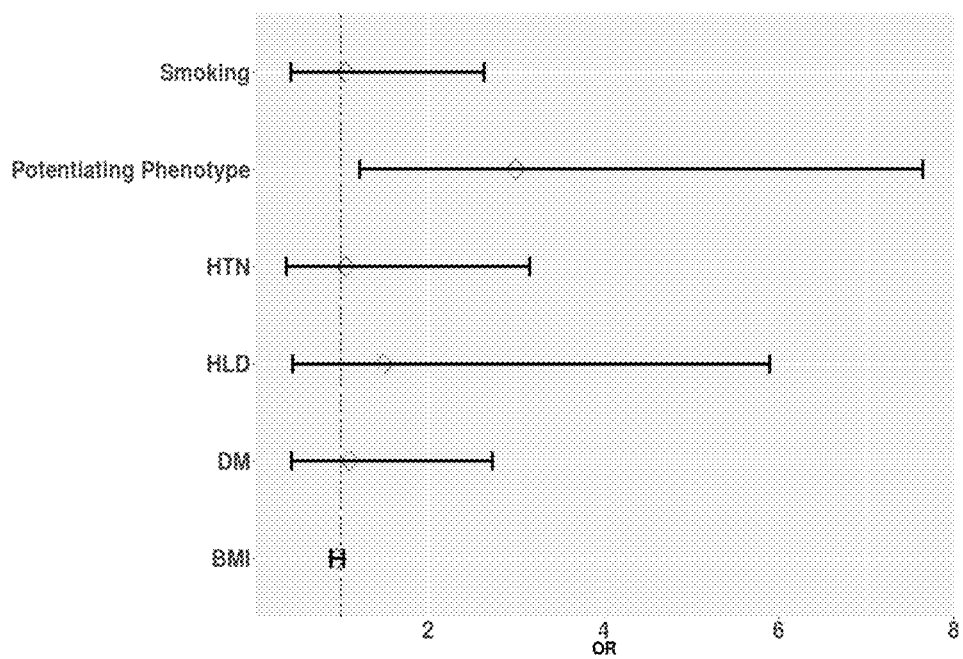
FIG. 4 includes odds ratios for STEMI, comparing potentiating phenotype to traditional risk factures, including smoking (current or past history), hypertension (HTN), hyperlipidemia (HLD), diabetes mellitus (DM), and body mass index (BMI).

Results:

There were 86 patients enrolled in this study, with 76% (n=65) males. The mean age was 61 years. Traditional CV risk factors were similar between the two phenotype groups (Table 1). In subjects with no STEMI, 66% had the inhibitory phenotype as compared to 39% of those with STEMI (FIG. 3, Chi-square=5.8, df=1, p=0.016). The comparison of odds ratios for STEMI based on traditional CV risk factors and PGE2 response phenotype in this at risk population is depicted in FIG. 4. As seen in FIG. 4, the potentiating phenotype was a significant risk factor for STEMI (OR=3.0, 95% CI=1.2, 7.6). No other significant relationships between traditional CV risk factors and STEMI were detected in the high-risk population.

TABLE 1

Clinical characteristics of patients with the inhibitory and potentiating phenotypes

| Characteristic | Inhibitory (n = 48) | Potentiating (n = 38) | P-value |
|---|---|---|---|
| Age (yrs)† | 61 ± 11.0 | 62 ± 12.0 | 0.81 |
| Male Sex° | 38 (79%) | 27 (71%) | 0.38 |
| Body mass index (kg/m²)† | 29.4 ± 6.9 | 30.4 ± 5.2 | 0.29 |
| Hypertension° | 35 (73%) | 31 (82%) | 0.34 |
| Hyperlipidemia° | 39 (81%) | 33 (87%) | 0.48 |
| Diabetes Mellitus° | 17 (35%) | 15 (40%) | 0.70 |
| Smoking° | 32 (67%) | 20 (53%) | 0.19 |

†mean ± standard dev.
°n (%)

Figure 5:
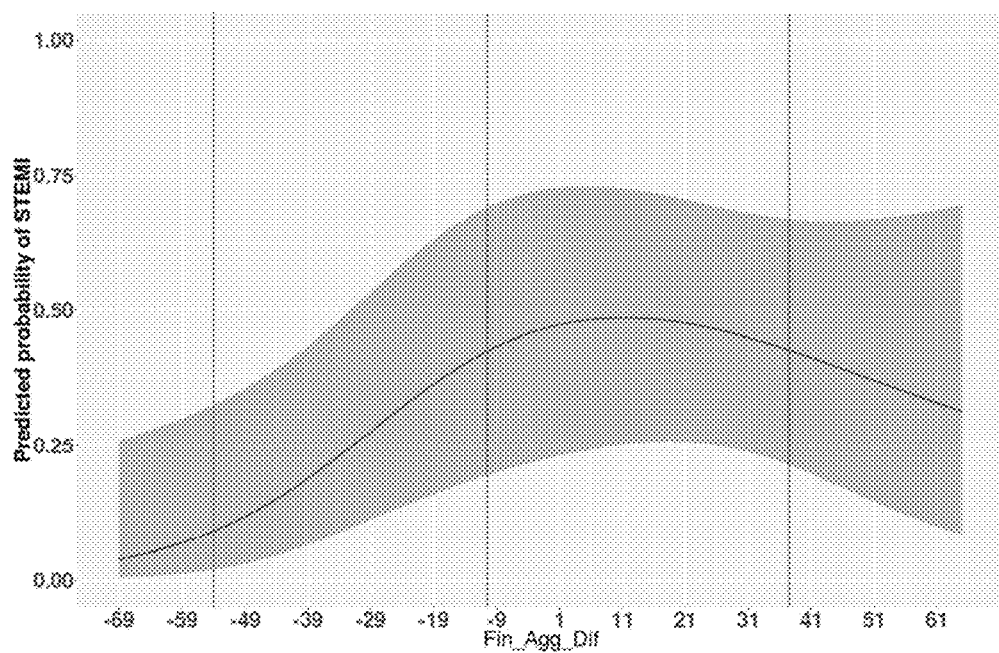
FIG. 5 includes a non-linear logistic regression of phenotype as continuous and STEMI.

A multiple logistic regression model was used to assess the association of the continuous phenotype, depicted as maximum aggregation difference, and STEMI, adjusting for smoking status and Diabetes Mellitus. Restricted cubic spline was applied to capture the non-linear relationship between phenotype and STEMI. The results suggested there was a marginally significant nonlinear trend (Chi-square=3, 67, df=1, p=0.056). As seen in FIG. 5, after adjusting for smoking status and Diabetes Mellitus, the predicted probabilities of STEMI increased from 0.04 (at the minimum of phenotype, −69) to 0.43 (at the median of phenotype, −10) and then decreased to 0.31 (at the maximum of phenotype, 65). The OR of phenotype at the median relative to that at the $10^{th}$ quantile was 7.4 (95% CI=1.6, 34.8), and the OR of phenotype at the $90^{th}$ quantile relative to that at the median was 1.0 (95% CI=0.38, 2.7).

Discussion

This study demonstrates that PGE2 response phenotype is independently associated with lifetime risk of STEMI. The inhibitory phenotype is protective with an odds ratio of 0.33 (95% CI=0.13, 0.82). In contrast, in this population, the traditional CV risk factors HTN, HLD, smoking and BMI were not able to distinguish between those patients who had or did not have a history of STEMI.

An EP3 antagonist can shift platelets from low threshold of activation to high threshold of activation. These results show that patients with the potentiating phenotype have about a 10-fold higher probability of developing STEMI than those with the inhibitory phenotype, and suggest that the PGE2 response phenotype may represent a novel CV risk factor. In addition, use of this risk factor could guide therapy with an EP3 antagonist.

STEMI is a consequence of plaque rupture that initiates a cascade of platelet activation, aggregation, and thrombus formation. When thrombus growth occludes the coronary artery, myocardial ischemia, injury, and necrosis ensue. Traditional risk assessment tools are not able to identify many patients at risk for STEMI, and in particular are not able to discriminate among patients who have known coronary artery disease [8-12]. Novel methods to refine this risk profile include identifying patients who have vulnerable plaque, susceptible myocardium, and pro-thrombotic tendencies, such as intrinsically lower thresholds to platelet activation. Ultimately, identifying these patients could lead to early targeted treatment.

Most research into platelet reactivity has centered on the responses to P2Y12 antagonists. Patients with high on-treatment platelet reactivity are at increased risk for primary and recurrent MI and overall cardiovascular mortality [4, 5, 13-15]. However, the mechanism of this risk, given that it is multifactorial, is not well understood. Frelinger et al. measured the active metabolite of clopidogrel and excluded subjects with polymorphisms in genes known to influence clopidogrel metabolism and concluded that unidentified factors contribute to high on-treatment platelet reactivity [16]. Markers of platelet activity such as P-selectin (soluble platelet selectin or CD62p) and PAC-1 (GPIIbIIIa receptor) correspond to in vitro platelet reactivity to agonists and may be linked to CV event risk, but have not been adopted into routine clinical practice [4, 15, 17, 18]. Clinical studies of using platelet reactivity assays to tailor antiplatelet therapy have not shown benefit [15, 16].

$PGE_2$, which is generated from macrophages in atherosclerotic plaques and during platelet activation, is increasingly recognized as a mediator of platelet reactivity [6, 19, 20]. PGE2 can either increase or decrease the platelet's activation threshold to agonists such as the thromboxane receptor agonist U46,619 [6] or the protease activated receptor 4 (PAR 4) specific agonist peptide [21]. The phenotype is determined by the relative activation of the $PGE_2$ receptor subtypes EP3 and EP4 [6]. In individuals with the inhibitory (high threshold) phenotype, local $PGE_2$ may hinder thrombus growth in response to vessel injury. In contrast, in individuals with the potentiating (low threshold) phenotype, platelet aggregation may be enhanced by the effects of $PGE_2$. This mechanism is consistent with the results showing that individuals with the high threshold phenotype are at lower risk for thrombotic events, such as STEMI.

Beyond being a novel risk prediction tool, determining $PGE_2$ response phenotype has implications for personalized antiplatelet therapy. When platelets from an individual with the low threshold phenotype are treated with the EP3 antagonist, DG-041, the phenotype shifts to high threshold [6] (FIG. 2). Thus, the drug may be able to reclassify an individual from a higher risk to a lower risk group. The drug also has unique pharmacologic properties such that it might inhibit thrombosis without affecting hemostasis [22, 23]. A major limitation in recent studies of tailored antiplatelet therapy is that the approach to high on-treatment reactivity has been to use higher doses of P2Y12 inhibitors or higher potency agents, which leads to an increased risk of bleeding [24]. In contrast, an EP3 inhibitor may be able to modify thrombotic risk without affecting bleeding.

The study has several strengths. It introduces a new mechanism for platelet reactivity, based on response to $PGE_2$, a substance ubiquitous in platelets and atherosclerotic plaques. This study is also a model approach for translation of an in vitro platelet assay to a clinically meaningful endpoint. Finally, this study introduces a novel risk factor that may identify patients at high risk for STEMI in a population already at high overall risk for CV events. Limitations of the study include the relatively small sample size and the low specificity of the $PGE_2$ response phenotype for STEMI. However, there are no current risk factors for STEMI that have high specificity.

CONCLUSION

Lower risk for STEMI is observed in subjects with the inhibitory $PGE_2$ platelet phenotype. $PGE_2$ response phenotype is able to stratify an already high-risk group, based on accepted clinical risk factors. Thus, the $PGE_2$ phenotype may be a novel marker of cardiovascular risk that also guides precision prescribing using an EP3 antagonist. Future studies will include validating these findings with a larger cohort and a clinical trial using an EP3 antagonist tailored to individual phenotype.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Shuldiner, A. R., et al., *Association of cytochrome P450 2C19 genotype with the antiplatelet effect and clinical efficacy of clopidogrel therapy*. Jama, 2009. 302(8): p. 849-57.
2. Mega, J. L., et al., *Cytochrome p-450 polymorphisms and response to clopidogrel*. N Engl J Med, 2009. 360(4): p. 354-62.
3. Stone, G. W., et al., *Platelet reactivity and clinical outcomes after coronary artery implantation of drug-eluting stents (ADAPT-DES): a prospective multicentre registry study*. Lancet, 2013. 382(9892): p. 614-23.
4. Kabbani, S. S., et al., *Platelet reactivity characterized prospectively: a determinant of outcome 90 days after percutaneous coronary intervention*. Circulation, 2001. 104(2): p. 181-6.
5. Trip, M. D., et al., *Platelet hyperreactivity and prognosis in survivors of myocardial infarction*. New England Journal of Medicine, 1990. 322(22): p. 1549-54.
6. Smith, J. P., et al., $PGE_2$ *decreases reactivity of human platelets by activating EP2 and EP4*. Thrombosis Research, 2010. 126(1): p. e23-9.
7. Waxman, S., et al., *In vivo validation of a catheter-based near-infrared spectroscopy system for detection of lipid core coronary plaques: initial results of the SPECTACL study*. JACC Cardiovasc Imaging, 2009. 2(7): p. 858-68.
8. Ridker, P. M., et al., *Inflammation, aspirin, and the risk of cardiovascular disease in apparently healthy men*. N Engl J Med, 1997. 336(14): p. 973-9.
9. Sposito, A. C., et al., *Most of the patients presenting myocardial infarction would not be eligible for intensive lipid-lowering based on clinical algorithms or plasma C-reactive protein*. Atherosclerosis, 2011. 214(1): p. 148-50.
10. Thompson, S. G., et al., *Hemostatic factors and the risk of myocardial infarction or sudden death in patients with angina pectoris. European Concerted Action on Thrombosis and Disabilities Angina Pectoris Study Group*. N Engl J Med, 1995. 332(10): p. 635-41.
11. Motoyama, S., et al., *Computed tomographic angiography characteristics of atherosclerotic plaques subsequently resulting in acute coronary syndrome*. J Am Coll Cardiol, 2009. 54(1): p. 49-57.
12. Berry, J. D., et al., *Framingham risk score and prediction of coronary heart disease death in young men*. Am Heart J, 2007. 154(1): p. 80-6.
13. Fuster, V., et al., *The pathogenesis of coronary artery disease and the acute coronary syndromes (1)*. New England Journal of Medicine, 1992. 326(4): p. 242-50.
14. Fuster, V., et al., *The pathogenesis of coronary artery disease and the acute coronary syndromes (2)*. New England Journal of Medicine, 1992. 326(5): p. 310-8.
15. Kabbani, S. S., et al., *Usefulness of platelet reactivity before percutaneous coronary intervention in determining cardiac risk one year later*. American Journal of Cardiology, 2003. 91(7): p. 876-8.
16. Frelinger, A. L., 3rd, et al., *Clopidogrel pharmacokinetics and pharmacodynamics vary widely despite exclusion or control of polymorphisms (CYP2C19, ABCB1, PON1), noncompliance, diet, smoking, co-medications (including proton pump inhibitors), and pre-existent variability in platelet function*. J Am Coll Cardiol, 2013. 61(8): p. 872-9.
17. Ridker, P. M., J. E. Buring, and N. Rifai, *Soluble P-selectin and the risk of future cardiovascular events*. Circulation, 2001. 103(4): p. 491-5.
18. Thomas, M. R., et al., *A platelet P-selectin test predicts adverse cardiovascular events in patients with acute coronary syndromes treated with aspirin and clopidogrel*. Platelets, 2014. 25(8): p. 612-8.
19. Iyu, D., et al., *PGE1 and PGE2 modify platelet function through different prostanoid receptors*. Prostaglandins Other Lipid Mediat, 2011. 94(1-2): p. 9-16.
20. Schober, L. J., et al., *The role of PGE(2) in human atherosclerotic plaque on platelet EP(3) and EP(4) receptor activation and platelet function in whole blood*. J Thromb Thrombolysis, 2011. 32(2): p. 158-66.
21. Friedman, E. A., et al., *Understanding the role of prostaglandin E2 in regulating human platelet activity in health and disease*. Thromb Res, 2015. 136(3): p. 493-503.
22. Tilly, P., et al., Blocking the EP3 receptor for PGE2 with DG-041 decreases thrombosis without impairing haemostatic competence. Cardiovasc Res, 2014. 101(3): p. 482-91.
23. Fox, S. C., et al., Effects on platelet function of an EP3 receptor antagonist used alone and in combination with a P2Y12 antagonist both in-vitro and ex-vivo in human volunteers. Platelets, 2013. 24(5): p. 392-400.
24. Tantry, U.S., et al., Consensus and update on the definition of on-treatment platelet reactivity to adenosine diphosphate associated with ischemia and bleeding. J Am Coll Cardiol, 2013. 62(24): p. 2261-73.

25. Rieber, J., et al., *Diagnostic accuracy of optical coherence tomography and intravascular ultrasound for the detection and characterization of atherosclerotic plaque composition in ex-vivo coronary specimens: a comparison with histology.* Coron Artery Dis, 2006. 17(5): p. 425-30.
26. Folsom, A. R., et al., *Association of hemostatic variables with prevalent cardiovascular disease and asymptomatic carotid artery atherosclerosis. The Atherosclerosis Risk in Communities (ARIL) Study Investigators.* Arterioscler Thromb, 1993. 13(12): p. 1829-36.
27. Gong, L. L., et al., *Association of tissue plasminogen activator and plasminogen activator inhibitor polymorphism with myocardial infarction: a meta-analysis.* Thromb Res, 2012. 130(3): p. e43-51.
28. Ardissino, D., et al., *Prothrombotic genetic risk factors in young survivors of myocardial infarction.* Blood, 1999. 94(1): p. 46-51.
29. O'Gara, et al., 2013 *ACCF/AHA Guidelines for the Management of ST-Elevation Myocardial Infarction,* J. Am. College of Cardiology, 2013. 61(61): e78-140.
30. Levine, et al., 2015 *ACC/AHA/SCAT Focused Update on Primary Percutaneous Coronary Intervention for Patients with ST-Elevation Myocardial Infarction,* J. Am. College of Cardiology, 2015. 67(10): 1235-1250.
31. Greenland, et al., 2010 *ACCF/AHA Guideline for Assessment of Cardiovascular Risk in Asymptomatic Adults,* J. Am. College of Cardiology, 2010. 56(25): e50-103.
32. Eckel, et al., 2013 *AHA/ACC Guideline Lifestyle Management to Reduce Cardiovascular Risk,* J. Am. College of Cardiology, 2014. 63(25): 2960-84.
33. Levine, et al., 2015 *ACC/AHA/SCAI Focused Update on Primary Percutaneous Coronary Intervention for Patients with ST-Elevation Myocardial Infarction,* 2016. 67(10): 1235-1250.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of identifying an increased risk of developing ST-Segment Elevation Myocardial Infarction (STEMI) in a subject, comprising:
    (a) obtaining a platelet-containing plasma sample from the subject;
    (b) determining a Prostaglandin E2 (PGE2) phenotype of the platelets of the subject by
        (i) contacting a first portion of the plasma sample with a thromboxane agonist;
        (ii) contacting a second portion of the plasma sample with the thromboxane agonist and PGE2;
        (iii) comparing the platelet aggregation in the first portion of the plasma sample to the platelet aggregation in the second portion of the plasma sample; and
        (iv) identifying the subject as having an inhibitory phenotype if the PGE2 inhibits platelet aggregation, or identifying the subject as having a potentiating phenotype if the PGE2 potentiates platelet aggregation; and
    (c) identifying the subject has having an increased risk of developing STEMI when the subject has a potentiating phenotype, as compared to the risk of a subject having an inhibitory phenotype.

2. The method of claim 1, and when the subject has a potentiating phenotype, further comprising:
    (a) contacting a third portion of the plasma sample with an EP3 antagonist and the thromboxane agonist;
    (b) contacting a fourth portion of the plasma sample with the EP3 antagonist, the thromboxane agonist, and PGE2;
    (c) comparing the platelet aggregation in the third portion of the plasma sample to the platelet aggregation in the fourth portion of the plasma sample; and
    (d) determining whether the potentiating phenotype has shifted to an inhibitory phenotype.

3. The method of claim 2, and further comprising identifying the subject as being a candidate for treatment when the potentiating phenotype shifts to an inhibitory phenotype.

4. The method of claim 3, and further comprising administering treatment to the subject.

5. The method of claim 4, wherein treatment includes administering an EP3antagonist.

6. The method of claim 5, wherein the EP3 antagonist is DG-041.

7. The method of claim 2, and further comprising excluding the subject as a candidate for treatment when the potentiating phenotype does not shift to an inhibitory phenotype.

8. The method of claim 2, wherein the EP3 antagonist is selected from the group consisting of: L-826266, ONO-AE3-240, L-798,106, L-826266, ONO-AE2-227, ONO-AE3-208, ONO-8711, SC-51322, AH6809, ONO-8713, ONO-AE5-599,ONO-AE3-240, ONO-AE2-227, and DG-041.

* * * * *